(12) United States Patent
Sugimoto et al.

(10) Patent No.: US 7,632,227 B2
(45) Date of Patent: Dec. 15, 2009

(54) ELECTRONIC ENDOSCOPE SYSTEM

(75) Inventors: Hideo Sugimoto, Tokyo (JP);
Mitsufumi Fukuyama, Tokyo (JP)

(73) Assignee: Hoya Corporation, Tokyo (JP)

( * ) Notice: Subject to any disclaimer, the term of this patent is extended or adjusted under 35 U.S.C. 154(b) by 722 days.

(21) Appl. No.: 11/275,397

(22) Filed: Dec. 29, 2005

(65) Prior Publication Data
US 2006/0149133 A1    Jul. 6, 2006

(30) Foreign Application Priority Data
Jan. 5, 2005    (JP) .............................. 2005-000947

(51) Int. Cl.
*A61B 1/06* (2006.01)
(52) U.S. Cl. ...................... 600/160; 600/109; 600/118; 348/65
(58) Field of Classification Search ................. 600/109, 600/118, 160, 178, 181, 476–477; 348/65, 348/68, 73, 74
See application file for complete search history.

(56) References Cited

U.S. PATENT DOCUMENTS

| | | | |
|---|---|---|---|
| 5,357,580 A * | 10/1994 | Forestieri et al. ............ | 382/128 |
| 5,749,830 A * | 5/1998 | Kaneko et al. .............. | 600/160 |
| 6,099,466 A | 8/2000 | Sano et al. | |
| 7,050,086 B2 * | 5/2006 | Ozawa ........................ | 348/70 |
| 7,082,224 B2 * | 7/2006 | Ikeda et al. ................. | 382/278 |
| 2002/0026099 A1 * | 2/2002 | Adachi et al. ............... | 600/178 |
| 2004/0135922 A1 * | 7/2004 | Nakajima et al. ........... | 348/362 |
| 2004/0143157 A1 * | 7/2004 | Doguchi et al. ............. | 600/109 |
| 2004/0210107 A1 * | 10/2004 | Tani et al. ................... | 600/109 |

(Continued)

FOREIGN PATENT DOCUMENTS

| | | |
|---|---|---|
| JP | 9-66023 | 3/1997 |
| JP | 2003-33324 | 2/2003 |

OTHER PUBLICATIONS

English language Abstract of JP 9-66023, Nov. 1997.
U.S. Appl. No. 11/275,418 to Fukuyama et al., which was filed on Dec. 30, 2005.

*Primary Examiner*—John P Leubecker
*Assistant Examiner*—Samuel Candler
(74) *Attorney, Agent, or Firm*—Greenblum & Bernstein P.L.C.

(57) ABSTRACT

An electronic endoscope system used for observing living tissues inside a body cavity includes a single imaging device configured to output image signals corresponding to a received optical image, an illuminating apparatus having a white light source emitting white light and an excitation light source emitting excitation light, an image forming system configured to form the optical image of the living tissues illuminated with each of the white light and the excitation light on the imaging device, a display device, an image processing system that receives the image signals output from the single imaging device, the image processing system transforming the received image signals into signals which are allowed to be displayed on the display device, and a control system configured to control the whole of the electronic endoscope system, the image processing system employs image signals, obtained from an image, output from the single imaging device as a first field of image signals of an interlaced image, and employs image signals obtained by performing an arithmetical operation for image signals, obtained from a plurality of images, output from the single imaging device as a second field of image signals of the interlaced image.

20 Claims, 9 Drawing Sheets

U.S. PATENT DOCUMENTS

| | | |
|---|---|---|
| 2005/0020879 A1* | 1/2005 | Suzuki ........................ 600/118 |
| 2005/0054916 A1* | 3/2005 | Mostafavi ................... 600/427 |
| 2005/0288553 A1 | 12/2005 | Sugimoto |
| 2005/0288556 A1 | 12/2005 | Sugimoto |
| 2006/0020169 A1 | 1/2006 | Sugimoto |

* cited by examiner

ELECTRONIC ENDOSCOPE SYSTEM

BACKGROUND OF THE INVENTION

The present invention relates to an electronic endoscope system that is adapted to observe a fluorescence image of autofluorescence emitted from a body cavity wall irradiated with excitation light, as well as a normal image of the body cavity wall illuminated with white light, on a display device such as a monitor.

An example of such an electronic endoscope system is disclosed in Japanese Unexamined Patent Publication No. HEI 9-066023. FIG. 11 of the present application shows a configuration of an electronic endoscope system that is disclosed in FIG. 1 of Japanese Unexamined Patent Publication No. HEI 9-066023. The system includes a first solid-state imaging device 2A that takes a fluorescence image, and a second solid-state imaging device 3A that takes an RGB color image (normal image) with illuminating light using a frame sequential method. In the system, both signals outputted from the first and second solid-state imaging devices are processed by a video circuit 26A for a fluorescence image and a video circuit 24A for a normal images, respectively. The signals are then synthesized by an image synthesis circuit 28A to be displayed on a monitor device 40A. According to the operation of a display image selector switch 29A, one of the two kinds of images or both is displayed on the monitor device 40A.

An additional example of an electronic endoscope system is disclosed in Japanese Unexamined Patent Publication No. P2003-33324A. FIG. 12 of the present application shows a block diagram of the system that is illustrated in FIG. 16 of Japanese Unexamined Patent Publication No. P2003-33324A. The system disclosed in Japanese Unexamined Patent Publication No. P2003-33324A includes (see FIG. 12) a first lamp 124 that emits illuminating light for normal observation and a second lamp 125 that emits excitation light, and either one of the two kinds of light is selectively introduced into a light guide 133 by changing the position of a movable mirror 128. Image signals captured by CCD 137 are stored in a first memory 141 and a second memory 142, and are then displayed on a Hi-Vision monitor 115 through a display location selector circuit 144. When a selector switch 135 for displaying two images (hereinafter, referred to as a two-image-display switch) is turned ON, a normal image and a fluorescence image are displayed on the Hi-Vision monitor 115, simultaneously. That is to say, when the two-image-display switch is turned ON, the mirror 128 is turned to a position indicated by a solid line, so that the excitation light is introduced to the light guide 133. At the same time, the first memory becomes write-protected, and a normal image, inputted thereto immediately before that, is outputted repeatedly to provide a still image. On the other hand, after the excitation light is irradiated for a predetermined time period, a shutter 132 is closed, and fluorescence image signals taken during the time period are stored in the second memory 142. Then, the second memory 142 becomes write-protected, and thereafter, the fluorescence image signals stored in the second memory are outputted repeatedly to be displayed as a still image. The mirror 28 is then turned back to a position shown by a dotted line, and the shutter is opened. Thereby, normal images, taken with the illuminating light emitted from the first lamp 124, are sequentially stored in the first memory 141, so that the normal image is displayed as a moving image.

However, the system, shown in FIG. 11, has to be provided with the two imaging devices for the normal image and fluorescence image at the distal end portion of the endoscope. Compared with the case of a single imaging device being used, employing two imaging devices of the same size as that of the single device in the above case causes a larger diameter of the distal end portion. On the other hand, employing the same diameter of the distal end portion as the above case causes a smaller size of each of the imaging devices, which results in a higher cost of the system due to a reduced pixel size of each of the imaging devices, or a lower resolution due to a reduced number of pixels.

On the contrary, by employing such a configuration as shown in FIG. 12, it is possible to take both of the normal image and fluorescence image with a single imaging device. However, both of the images are selectively obtained by changing the movable mirror 128. Therefore, for example, since it is impossible to display both of the images as moving images simultaneously, it is not allowed to compare and observe the moving images of both of the images.

It is noted that when displaying the moving images of both of the normal image and fluorescence image simultaneously with a single imaging device, it is necessary to repeat a cycle of predetermined periods of taking both of the normal image and fluorescence image. As a result, since amount of information of each of both of the image signals is reduced by half in comparison with the case of taking only one of both of the images, both of the images are displayed with reduced resolutions.

SUMMARY OF THE INVENTION

The present invention is advantageous in that an electronic endoscope system is provided that is capable of keeping resolutions of both of a fluorescence image and a normal image from being reduced while displaying both of the images simultaneously with a single imaging device.

According to an aspect of the invention, there is provided an electronic endoscope system used for observing living tissues inside a body cavity, which includes a single imaging device configured to receive an optical image and output image signals obtained from the optical image, an illuminating apparatus having a white light source emitting white light and an excitation light source that emits excitation light having a predetermined wavelength, the living tissues emitting autofluorescence when irradiated with the excitation light, an image forming system configured to form the optical image of the living tissues illuminated with each of the white light and the excitation light on the imaging device, a display device, an image processing system that receives the image signals outputted from the single imaging device, the image processing system transforming the received image signals into signals which are allowed to be displayed on the display device, and a control system configured to control the whole of the electronic endoscope system. The control system controls the illuminating apparatus to illuminate the living tissues alternately with the white light and excitation light. The control system controls the image processing system to obtain normal image signals when the living tissues are illuminated with the white light and fluorescence image signals when the living tissues are irradiated with the excitation light. The image processing system employs image signals, obtained from an image, outputted from the single imaging device as a first field of image signals of an interlaced image, and employs image signals obtained by performing an arithmetical operation for image signals, obtained from a plurality of images, outputted from the single imaging device as a second field of image signals of the interlaced image. One frame of each of the normal image and fluorescence image is configured with the first field of image signals and the second field of image signals.

Optionally, the image processing system may employ image signals obtained by averaging the image signals obtained from the plurality of images outputted from the single imaging device as the second field of image signals of the interlaced image.

Optionally, the image processing system may include, for each of the normal image and fluorescence image, a first image memory configured to store image signals obtained from an image outputted from the single imaging device, at least one delay system configured to receive the image signals outputted from the first image memory and output the image signals with a predetermined period of delay, an arithmetic system configured to perform said arithmetical operation for the image signals outputted from the first image memory and the image signals outputted from the at least one delay system, the arithmetic system outputting the modified image signals by the arithmetical operation, a second image memory configured to store the modified image signals outputted from the arithmetic system, and a switch configured to select image signals to be outputted from the image signals outputted from the first image memory and the modified image signals outputted from the second image memory.

Still optionally, the image processing system may employ image signals obtained by averaging image signals obtained from an image outputted from the single imaging device in the last cycle and image signals obtained from an image outputted from the single imaging device in the cycle before the last cycle as the second field of image signals of the interlaced image.

Alternatively or optionally, the image processing system may include, for each of the normal image and fluorescence image, a first image memory configured to store image signals obtained from an image outputted from the single imaging device, at least one delay system configured to receive the image signals outputted from the first image memory and output the image signals with a predetermined period of delay, an averaging system configured to perform an averaging operation for the image signals outputted from the first image memory and the image signals outputted from the at least one delay system, the averaging system outputting the averaged image signals by the averaging operation, a second image memory configured to store the averaged image signals outputted from the averaging system, and a switch configured to select image signals to be outputted from the image signals outputted from the first image memory and the averaged image signals outputted from the second image memory.

Alternatively or optionally, the image processing system may include, for each of the normal image and fluorescence image, a first image memory configured to store image signals obtained from an image outputted from the single imaging device, a delay system configured to receive the image signals outputted from the first image memory and output the image signals with a period of delay corresponding to one frame, an averaging system configured to perform an averaging operation for the image signals outputted from the first image memory and the image signals outputted from the delay system, the averaging system outputting the averaged image signals by the averaging operation, a second image memory configured to store the averaged image signals outputted from the averaging system, and a switch configured to select image signals to be outputted from the image signals outputted from the first image memory and the averaged image signals outputted from the second image memory.

Optionally, the image processing system may further include a pre-signal-processing system configured to process the image signals received from the single imaging device, the processed image signals being inputted to the first image memory, and a post-signal-processing system, for each of the normal image and fluorescence image, configured to transform the image signals outputted from the switch into signals which are allowed to be displayed on the display device.

Optionally, the illuminating apparatus may include a rotary shutter provided in front of the white light source, the rotary shutter having a light transmitting area and a light blocking area, the white light intermittently illuminating the living tissues as the rotary shutter rotates.

Further optionally, the illuminating apparatus may include an excitation light source driver that intermittently turns on/off the excitation light source synchronously with the blocking/transmitting operation of the rotary shutter.

Optionally, the rotary shutter may be able to be shifted integrated with a beam combiner to a point where the rotary shutter does not interfere with the white light, the beam combiner combining both light paths of the white light and the excitation light.

Optionally, the image forming system may include an objective lens configured to receive light from the living tissues and forms an image thereof, and an excitation light cut filter provided between the objective lens and the imaging device. Optionally, the excitation light cut filter may eliminate the wavelength components equivalent to the excitation light from light directed to the imaging device from the objective lens.

Preferably, the excitation light source may emit near-ultraviolet light.

BRIEF DESCRIPTION OF THE
ACCOMPANYING DRAWINGS

Figure 11:
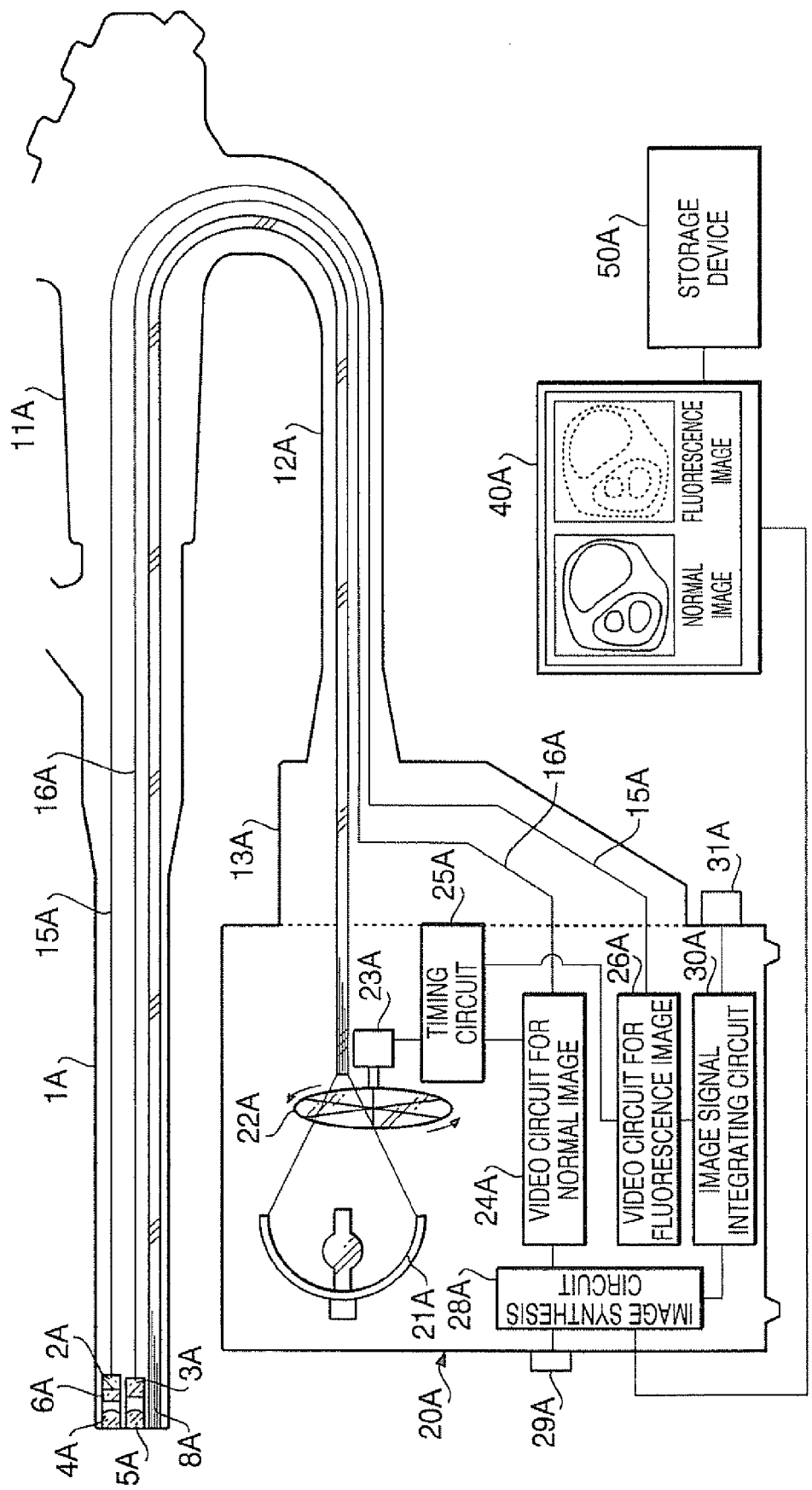
Figure 12:
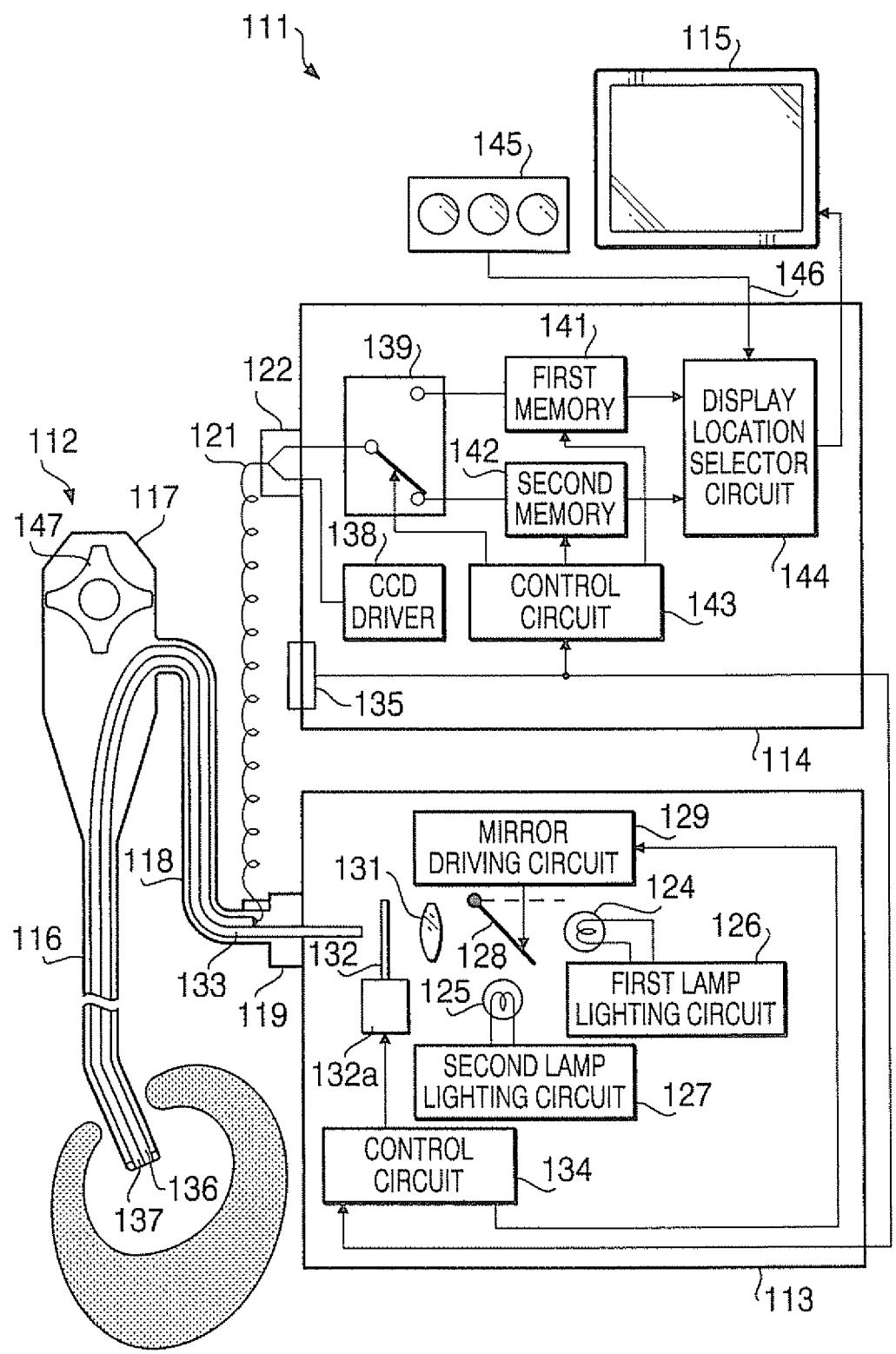

FIG. 11 schematically shows a configuration of a conventional electronic endoscope system; and FIG. 12 schematically shows a configuration of another conventional electronic endoscope system.

DETAILED DESCRIPTION OF THE EMBODIMENTS

Hereinafter, an electronic endoscope system according to an embodiment of the present invention will be described with reference to the accompanying drawings. The electronic endoscope system of the embodiment is directed to a system that is adapted to observe a fluorescence image of autofluorescence emitted from a body cavity wall irradiated with excitation light on a display device such as a monitor, as well as a normal image of the body cavity wall illuminated with white light.

Figure 1:
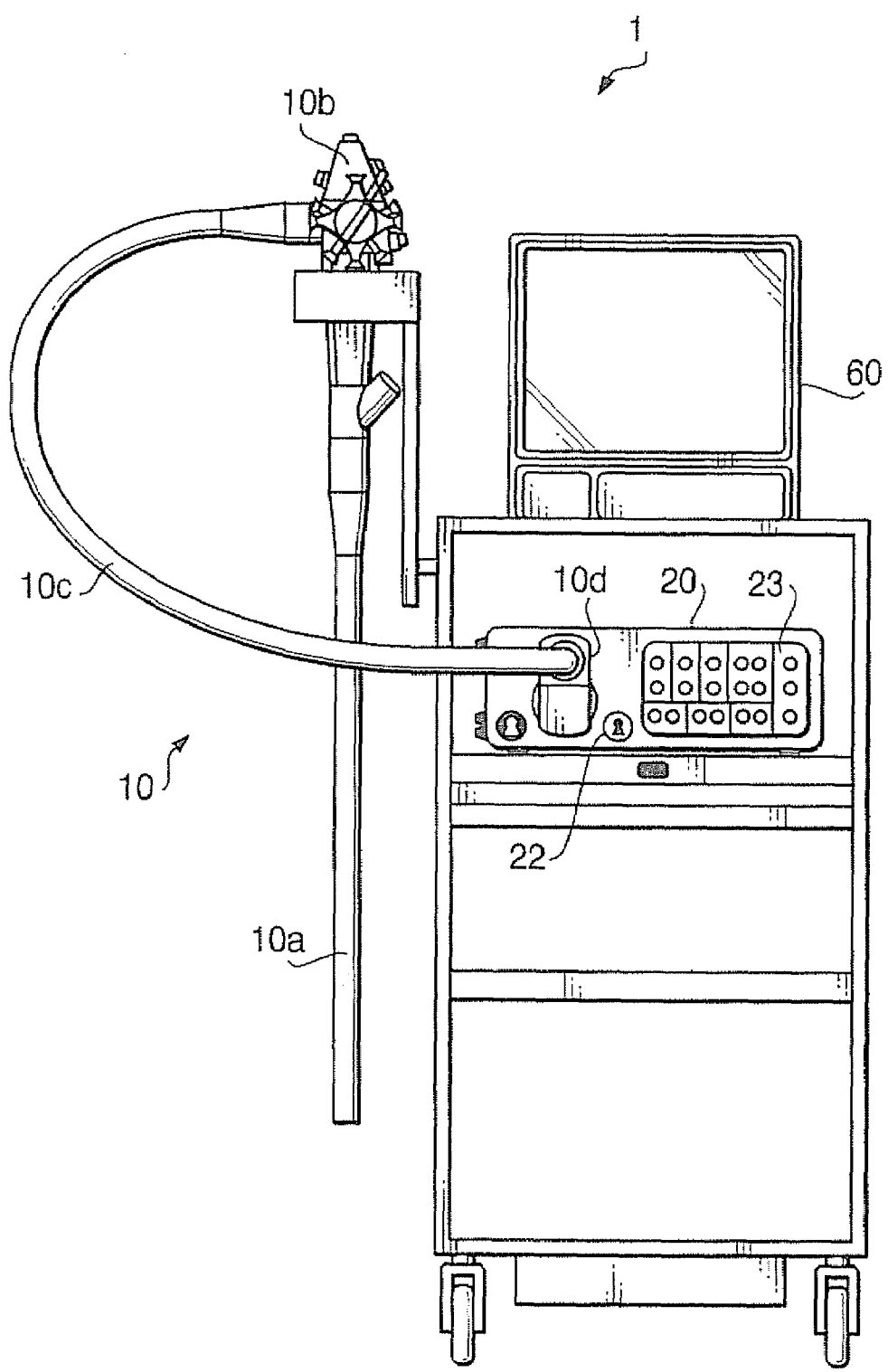
FIG. 1 is a front view of an electronic endoscope system according to an embodiment of the present invention.
Figure 2:
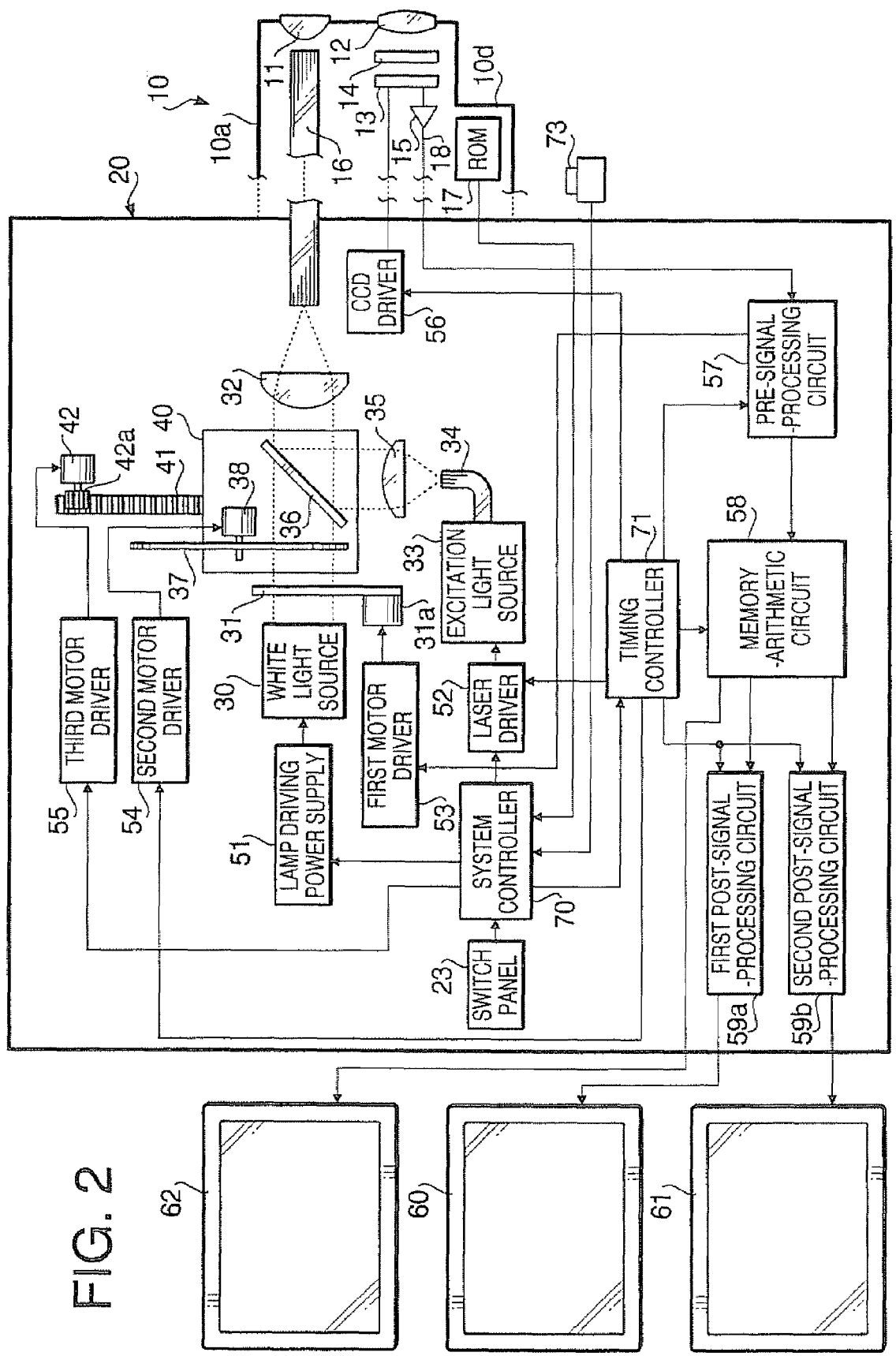
FIG. 2 is a block diagram illustrating an internal configuration of the electronic endoscope system shown in FIG. 1.

FIG. 1 schematically shows an external view of an electronic endoscope system 1 according to an embodiment of the present invention. FIG. 2 shows a block diagram illustrating an internal configuration of the electronic endoscope system 1. As shown in FIG. 1, the electronic endoscope system 1 is provided with a fluorescence observation endoscope 10, a light source apparatus 20, and a monitor 60. It is noted that the system 1 of the embodiment, as shown in FIG. 2, includes a first television monitor 60, a second television monitor 61, a high-definition monitor 62, yet only the single monitor 60, on behalf of the above three monitors, is shown in FIG. 1.

The fluorescence observation endoscope 10, which is obtained by modifying a usual electronic endoscope so as to be adapted for fluorescence observation, is provided with an insertion part 10a that is formed long and slender so as to be inserted into the body cavity and has a flexible bendable part at the tip thereof, an operating part 10b that includes an angle knob and the like to operate the bendable part of the insertion part 10a, a flexible light guide tube 10c that connects the operating part 10b with a light source apparatus 20, and a connector 10d that is provided at the rear anchor of the flexible light guide tube 10c.

The light source apparatus 20 supplies illuminating light and excitation light to the fluorescence observation endoscope 10, and, as described in detail below, has a function as a video signal generator that generates video signals from image signals taken by the fluorescence observation endoscope 10 and a function as a controlling means that controls the fluorescence image and normal image which have been taken to be displayed based on a setting. On the front surface of the light source apparatus 20, there are provided a key switch 22 for an ON/OFF operation of a main power supply thereof, and a switch panel 23 on which various kinds of operation switches are arranged.

Hereinafter, referring to FIG. 2, particular constitutions of the fluorescence observation endoscope 10 and the light source apparatus 20 will be explained in sequence. On the distal end surface of the insertion part 10a of the fluorescence observation endoscope 10, there are provided a light distribution lens 11 and an objective lens 12. Inside the tip portion of the insertion part 10a, there are incorporated an imaging device 13 such as a CCD color imaging sensor that takes an object's color image formed by the objective lens 12, an excitation light cut filter 14 for eliminating wavelength components equivalent to the excitation light for fluorescence excitation from wavelength components of light directed to the imaging device 13 from the objective lens 12, and a cable driver 15 that amplifies image signals outputted from the imaging device 13.

Figure 3:
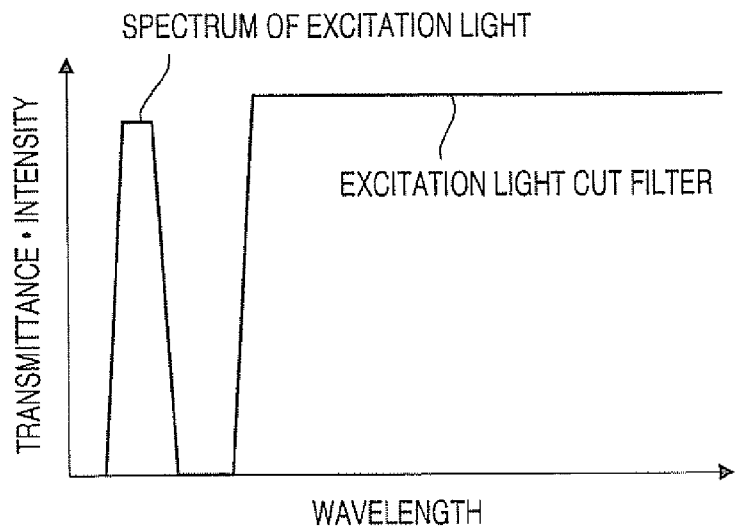
FIG. 3 is a graph illustrating transmission characteristics of an excitation light cut filter provided in an optical system in FIG. 2.

As shown in FIG. 3, the excitation light cut filter 14 has characteristics that cut off the excitation light and transmit light with wavelengths longer than the excitation light. Thereby, it is possible to prevent the excitation light from being incident onto the imaging device 13 and to take only the fluorescence images during fluorescence observation. It is noted that since near-ultraviolet light that excites autofluorescence of a living organism is applied as excitation light, even though the wavelength components of the excitation light is cut off by the excitation light cut filter 14, there is no trouble in taking blue components while taking normal color images.

A signal cable 18 that transmits the image signals amplified by the cable driver 15 runs through the insertion part 10a, the operating part 10b, and the flexible light guide tube 10c, and is connected to the below-mentioned circuit of the light source apparatus 20 that is connected to the fluorescence observation endoscope 10.

In parallel with the signal cable 18, a light guide 16, which is constituted by bundling a plurality of optical fibers, runs through the insertion part 10a, the operating part 10b, the flexible light guide tube 10c, and the connector 10d. The tip end face of the light guide 16 faces the light distribution lens 11 inside the tip portion of the insertion part 10a, and the rear anchor of the light guide 16 is fixed in the state of being inserted into the light source apparatus 20.

The light source apparatus 20 selectively introduces either white light for observation of the body cavity wall or the excitation light, which excites the living tissues of the body cavity wall such that the living tissues emits autofluorescence, into the end face of the rear anchor of the light guide 16. The light source apparatus 20 further processes the image signals received from the cable driver 15 to generate video signals, and then outputs the video signals to the first television monitor 60, the second television monitor 61, and the high-definition monitor 62. It is noted that the first television monitor 60 displays a moving normal image, the second television monitor 61 displays a moving fluorescence image, and the high-definition monitor 62 displays one or both, side by side, of the normal image and fluorescence image.

An optical system of the light source apparatus 20 is provided with a white light source (discharge tube lamp) 30 that emits substantially parallel visible light (white light), a light control aperture 31 that controls the beam diameter of the white light emitted from the white light source 30, a condenser lens 32 that converges the white light which is transmitted through the light control aperture 31 to be incident on the end face of the rear anchor of the light guide 16, an excitation light source (laser) 33 that emits the excitation light, an optical waveguide (single fiber) 34 that guides the excitation light emitted from the excitation light source 33, a collimating lens 35 that collimates the excitation light, which is diverging light emitted from the optical waveguide 34, and a dichroic mirror 36 that combines both light paths of the white light and the excitation light.

The light control aperture 31 is driven by an aperture driving motor 31a, and functions to control the intensity of the white light according to the reflectance of an object. The white light path that extends straight from the white light source 30 to the light guide 16 and the excitation light path that intersects perpendicularly therewith are combined by the light path combining device, i.e., the dichroic mirror 36. Since the dichroic mirror 36 transmits the visible light and reflects the near-ultraviolet light with wavelengths shorter than the visible light, the dichroic mirror 36 transmits major part of the white light and reflects the excitation light, introducing both kinds of light into a single light path that extends to the end face of the rear anchor of the light guide 16.

Figure 4:
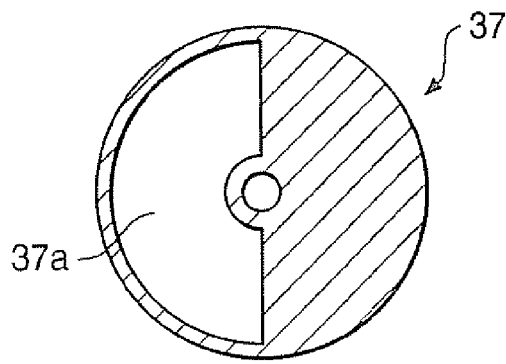
FIG. 4 is a front view of a rotary shutter provided in the optical system in FIG. 2.

Between the white light source 30 and the dichroic mirror 36, there is arranged a rotary shutter 37 that enables the intermittent ON/OFF operation of the white light (that is, intermittently transmits or blocks the white light). The rotary shutter 37, as a front view thereof is shown in FIG. 4, has a fan-shaped window 37a with a center angle of 180 degrees, and the size of the window 37a is configured to be larger than the diameter of the beam of the white light. The rotary shutter 37 is allowed to rotate and intermittently transmit the white light as a shutter driving motor 38 is driven.

In addition, the dichroic mirror 36, the rotary shutter 37, and the shutter driving motor 38 are arranged in a unit 40 that is movable in the up-and-down direction (a direction perpendicular to the white light path) in FIG. 2. A rack gear 41, extending along the moving direction thereof, is fixed to the unit 40, and is geared with a pinion 42a of a unit driving motor 42. Rotating the unit driving motor 42 allows the unit 40 to move integrally in the up-and-down direction, so that the dichroic mirror 36 and the rotary shutter 37 can be shifted between both positions on and off the white light path.

The light source apparatus 20 is provided with a lamp driving power supply 51 that supplies a current to the white light source 30, a laser driver 52 that drives and switches the excitation light source 33, a first motor driver 53 that drives the aperture driving motor 31a, a second motor driver 54 that drives the shutter driving motor 38, a third motor driver 55 that drives a unit driving motor 42, and a CCD driver 56 that drives the imaging device 13. The light source apparatus 20 further includes a pre-signal-processing circuit 57 that processes image signals received from the cable driver 15, a memory-arithmetic circuit 58 that stores and perform an arithmetical operation for the digital image signals processed by the pre-signal-processing circuit 57, a first and second post-signal-processing circuits 59a and 59b that transform the digital image signals after the arithmetical operation into standardized video signals which are allowed to be displayed on a television monitor and output the standardized video signals, and a system controller 70 and a timing controller 71 that control the whole of the above components.

The system controller 70 is connected with a fluorescence mode switch 73 provided at the operating part 10b of the fluorescence observation endoscope 10, and is further connected electrically with various switches that are arranged on the switch panel 23. Based on the setting of each of the switches, the system controller 70 controls the lamp driving power supply 51 and the laser driver 52, so that the white light and the excitation light are consecutively emitted or stopped, and also controls the third motor driver 55 that drives the unit driving motor 42 to shift the location of the unit 40, and further switches a display on the high-definition monitor 62. It is noted that the high-definition monitor 62 is configured to display not video signals as being displayed every frame or field on a television monitor but digital signals mapped on an image memory.

Figure 5:
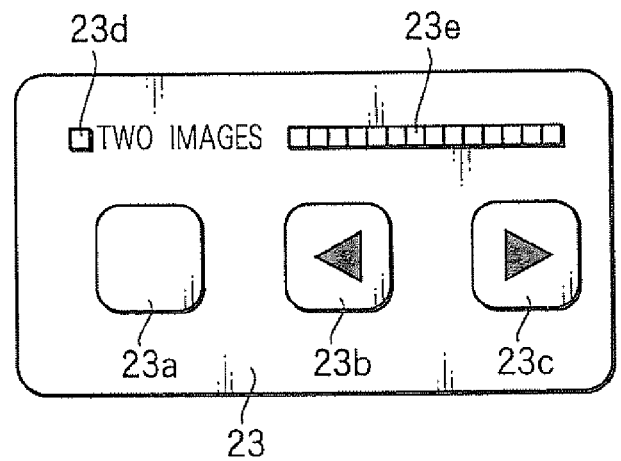
FIG. 5 is a schematic diagram illustrating constitution of a switch panel of the system shown in FIG. 2.

On the switch panel 23, as shown in FIG. 5, there are provided a fluorescence mode display button 23a for selecting either displaying only the fluorescence image or displaying both the fluorescence image and the normal image simultaneously side by side, in a fluorescence mode, and a pair of brightness setting buttons 23b and 23c for down/up, respectively. In addition, the switch panel 23 is provided with a two-image-indicator 23d which lights up when a mode of both the fluorescence image and the normal image being simultaneously displayed side by side is selected in the fluorescence mode and a setting level indicator 23e which visually indicates a target value for the brightness, of each of the fluorescence image and the normal image, set by operating the brightness setting buttons 23b and 23c.

When the fluorescence observation endoscope 10 is connected to the light source apparatus 20, the built-in ROM 17 inside the fluorescence observation endoscope 10 is connected to the system controller 70, which identifies the fluorescence observation endoscope 10 as being connected to the light source apparatus 20 by reading the identification data stored in the ROM 17.

Based on a command from the system controller 70, the timing controller 71 controls the laser driver 52 to carry out the intermittent ON/OFF operation of the excitation light at predetermined timing, and further controls the second motor driver 54 that drives the shutter driving motor 38 to carry out the intermittent ON/OFF operation of the white light at predetermined timing. The timing controller 71 also controls timing of the imaging device 13 taking an image through the CCD driver 56, and further instructs the pre-signal-processing circuit 57 and the memory-arithmetic circuit 58 on timing to process image signals. The pre-signal-processing circuit 57 controls the first motor driver 53 that drives the aperture driving motor 31a, so as to adjust the intensity of the white light, based on the brightness level of image signals inputted when taking the normal image, such that the normal image is displayed with appropriate brightness on each of the monitors 60 and 62.

Figure 6:
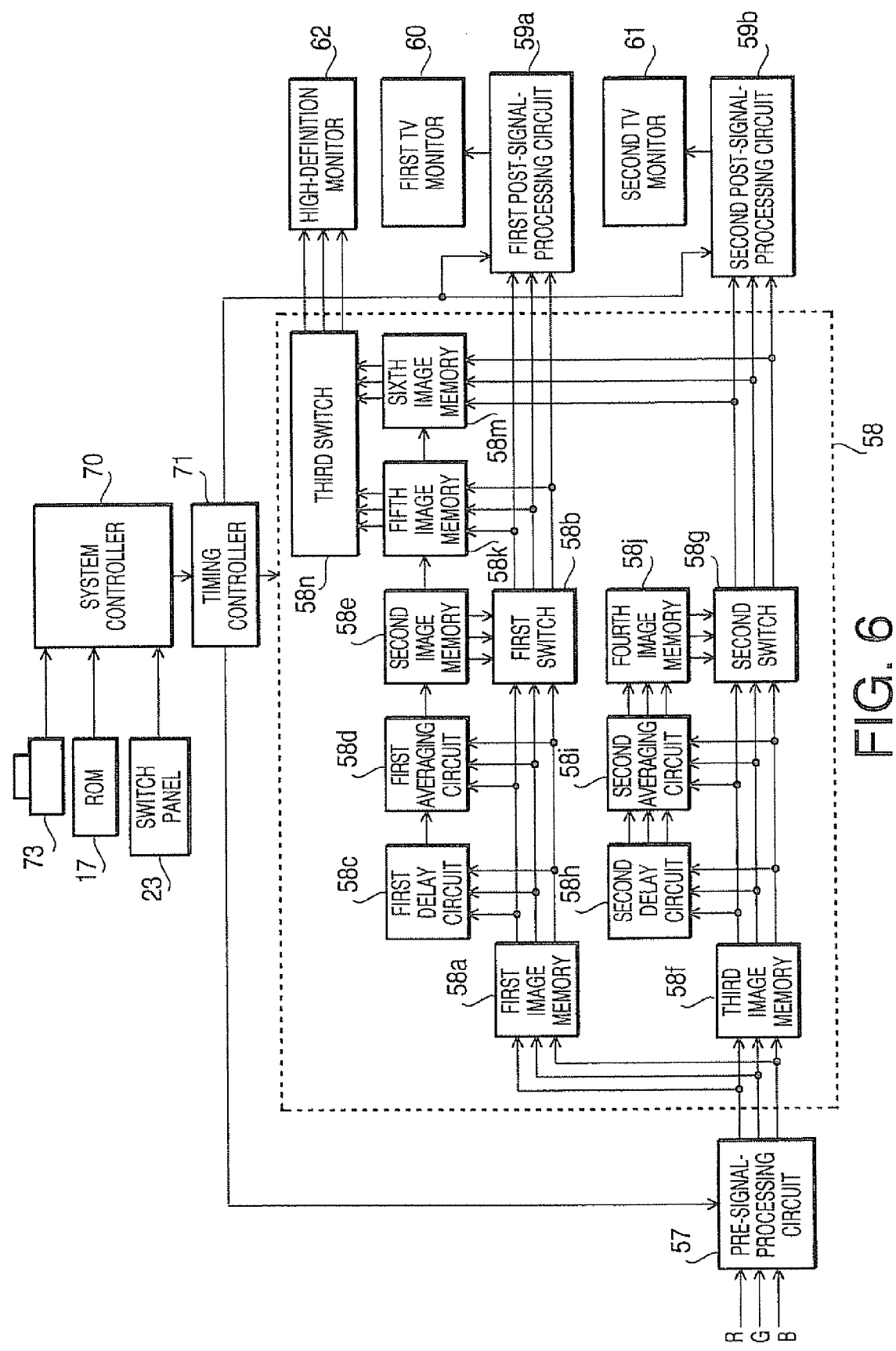
FIG. 6 is a block diagram illustrating a configuration of a memory-arithmetic circuit of the system shown in FIG. 2.

Next, the internal configuration of the memory-arithmetic circuit 58 will be explained with reference to a block diagram shown in FIG. 6. The configuration of the memory-arithmetic circuit 58 is divided into an upper stream, in FIG. 6, for processing the normal image and a lower stream for processing the fluorescence image. Among signals outputted from the pre-signal-processing circuit 57, normal image signals are stored in a first image memory 58a. The normal image signals stored in the first image memory 58a are then inputted to a first switch 58b, and are also inputted to a first delay circuit 58c and a first averaging circuit 58d. The first delay circuit 58c outputs the inputted normal image signals with a period of delay corresponding to one frame. The first averaging circuit 58d averages image signals taken in the previous cycle and the image signals taken in the last cycle, both of the image signals being outputted from the first delay circuit 58c, to be stored in a second image memory 58e. In other words, the normal image signals stored in the first image memory 58a, which are obtained from a taken image, will be signals corresponding to a first field of an interlaced image. The normal image signals stored in the second image memory 58e, which are obtained by performing the arithmetical operation for image signals of a plurality of images taken, will be signals corresponding to a second field of the interlaced image. Image signals corresponding to one frame of the normal image are configured with the signals of the first and second fields. The first switch 58b switches at predetermined timing between outputs from the first image memory 58a and the second image memory 58e to output the signals to the post-signal-processing circuit 59a.

The stream for the fluorescence image has a similar configuration to that for the normal image. Among signals outputted from the pre-signal-processing circuit 57, fluorescence image signals are stored in a third image memory 58f, and are inputted to a second delay circuit 58h and a second averaging circuit 58i, as well as a second switch 58g. The averaged fluorescence image signals are stored in a fourth image memory 58j. The second switch 58g switches at predetermined timing between outputs from the third image memory 58f and the fourth image memory 58j to output the signals to the second post-signal-processing circuit 59b.

In addition, the signals, outputted from the first switch 58b, corresponding to one frame of the normal image are stored in a fifth image memory 58k. The signals, outputted from the second switch 58g, corresponding to one frame of the fluorescence image are stored in a sixth image memory 58m.

These signals stored in the fifth and sixth image memories 58k and 58m are displayed on the high-definition monitor 62 via a third switch 58n. The third switch 58n makes the high-definition monitor 62 display one or both, side by side, of the moving normal image and moving fluorescence image based on settings of the switch panel 23 and the fluorescence mode switch 73.

Next, an operation of the electronic endoscope system, constituted as mentioned above, in the embodiment will be described. When a main switch of the system is turned on, the system controller 70 controls the lamp driving power supply 51 to make the white light source 30 continuously emit white light. The timing controller 71 controls the second motor driver 54 to rotate the shutter driving motor 38, and controls the laser driver D2 to turn off the excitation light source 33 while the window 37a of the rotary shutter 37 is being on the white light path (while the white light is being introduced into the light guide 16), and to turn on the excitation light source 33 while a light blocking area of the rotary shutter 37 is being on the white light path (while the white light is not being introduced into the light guide 16). Thereby, an object is irradiated alternately with the white light and the excitation light. The imaging device 13, provided at the distal end of the fluorescence observation endoscope 10, alternately takes the normal image of the body cavity wall illuminated with the white light and the fluorescence image of autofluorescence emitted from the body cavity wall irradiated with the excitation light. The image signals outputted from the imaging device 13 are inputted to the pre-signal-processing circuit 57 via the cable driver 15 and the signal cable 18.

Figure 7:
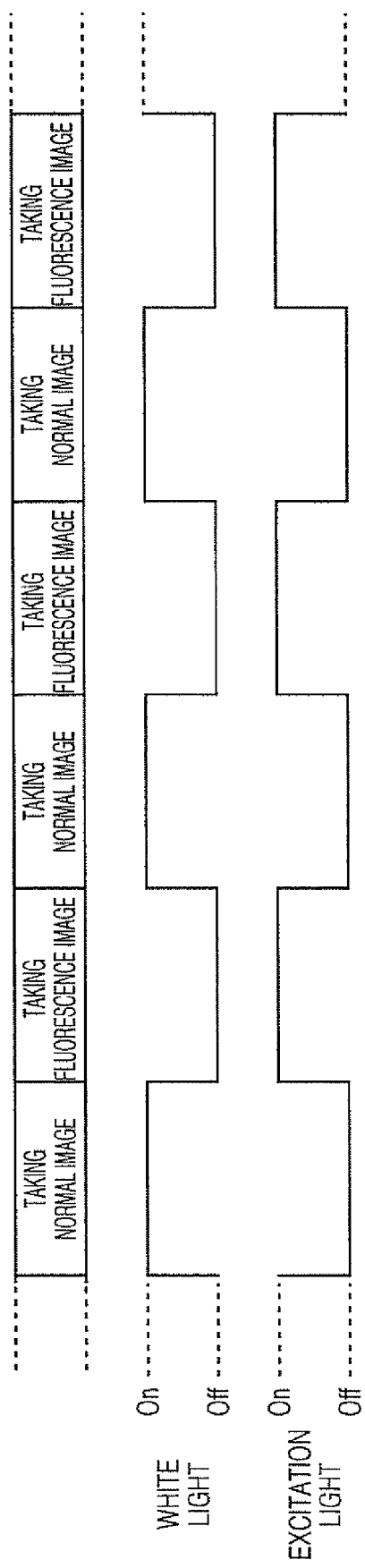
FIG. 7 is a chart illustrating the respective irradiation timings of white light and excitation light and the respective timings when the two kinds of image data are outputted from an imaging device.

FIG. 7 is a chart pattern showing the respective irradiation timings of the white light and the excitation light and the timing when image data is outputted from the imaging device 13. As shown in FIG. 7, the normal color image is taken while the white light is applied and the excitation light is not applied, and the fluorescence image is taken while the white light is not applied and the excitation light is applied.

Figure 8:
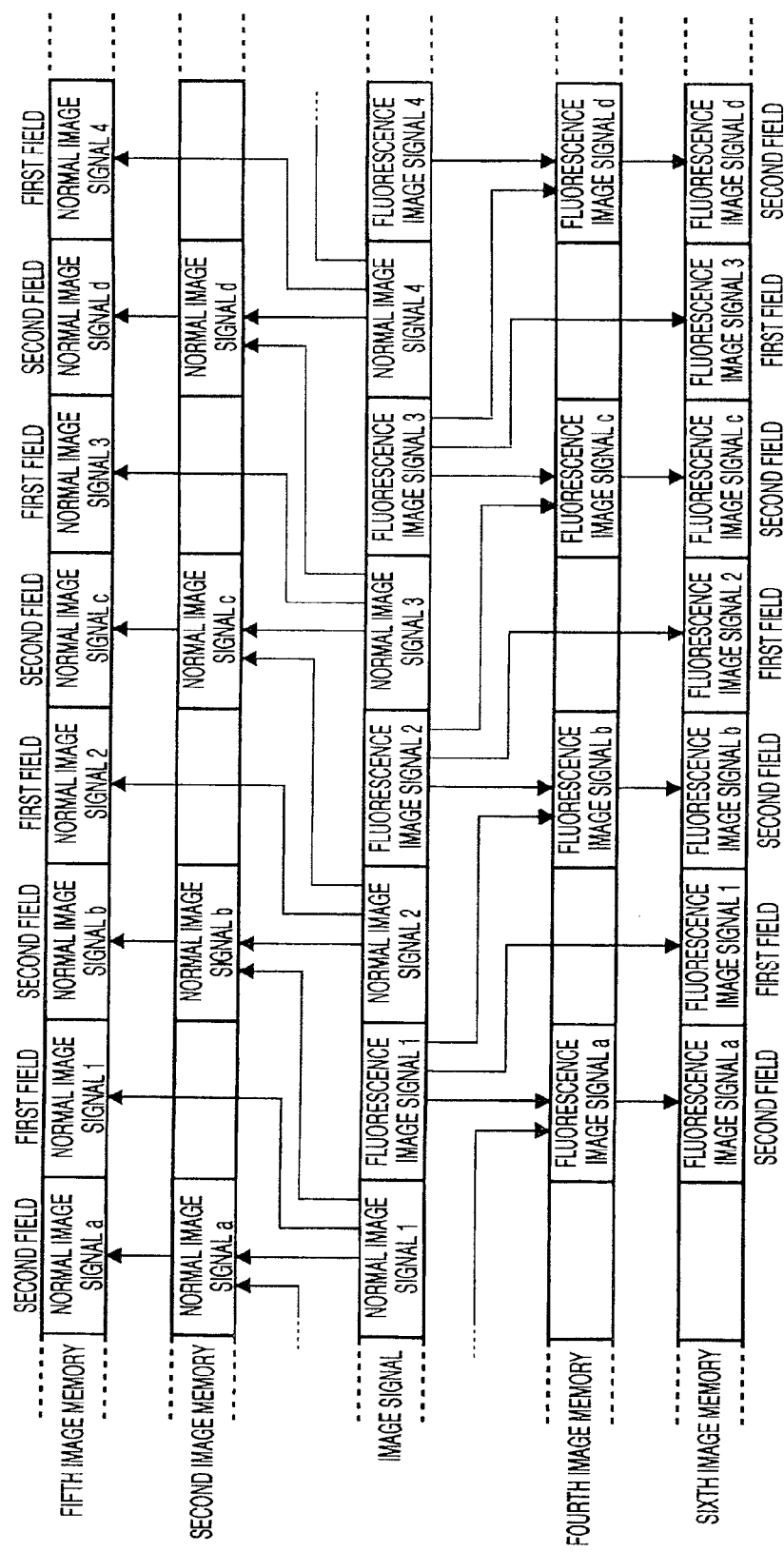
FIG. 8 is a timing chart illustrating processes of image signals in the memory-arithmetic circuit of the system shown in FIG. 2.

The memory-arithmetic circuit 58, as shown in a timing chart of FIG. 8, complements the second field of image signals of the normal image and fluorescence image with the arithmetical operation, and outputs the second field of image signals combined with the first field of image signals obtained from a taken image as a frame of image signals. In other words, normal image signals 1 outputted from the pre-signal-processing circuit 57 are stored in the first image memory 58a. The normal image signals are then outputted as the first field of image signals, with delay corresponding to one field, to the first post-signal-processing circuit 59a via the first switch 58b, while being stored in the fifth image memory 58k. In addition, the normal image signals 1 are delayed by a period of one frame (two fields) by the first delay circuit 58c. Thereafter, the first averaging circuit 58d provides an operation to average the normal image signals 1 and normal image signals 2 to be inputted in the next cycle. Normal image signals b after the averaging operation are stored in the second image memory 58e as the second field of image signals. The normal image signals b are outputted, as the second field of image signals, to the first post-signal-processing circuit 59a via the first switch 58b, following the normal image signals 1, while being stored in the fifth image memory 58k. Thus, the first field of image signals is outputted from the first image memory 58a without any operation, while the second field of image signals is outputted as a result of the averaging operation for two fields of image signals.

In a process of the fluorescence image signals, in the same way as mentioned above, the first field of image signals is outputted to the second post-signal-processing circuit 59b from the third image memory 58f without any operation, while being stored in the sixth image memory 58m. In addition, the second field of image signals is outputted to the second post-signal-processing circuit 59b as a result of the averaging operation for two fields of image signals, while being stored in the sixth image memory 58m.

Figure 9:
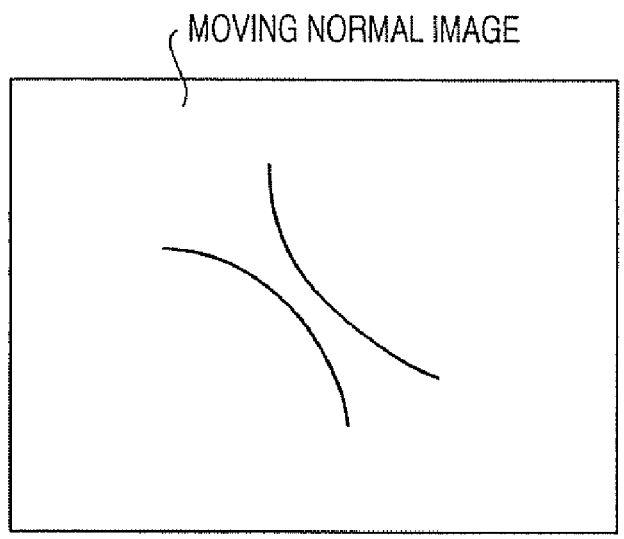
FIG. 9 is an example of a screen displayed on a high-definition monitor of the system shown in FIG. 2.
Figure 10:
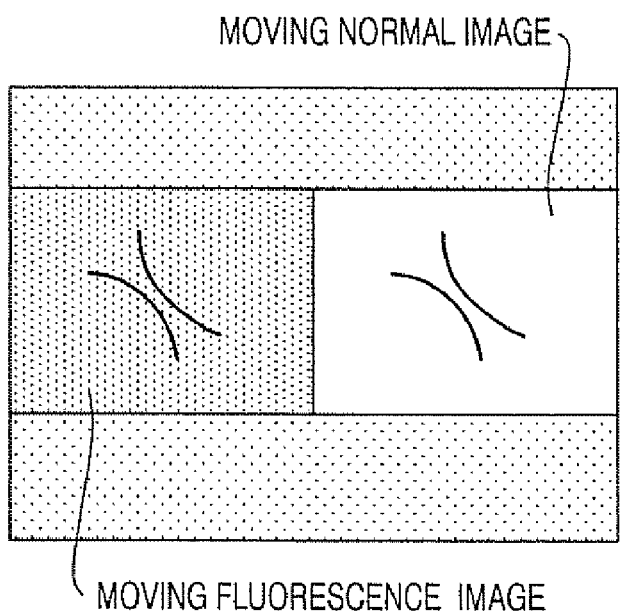
FIG. 10 is another example of a screen displayed on the high-definition monitor of the system shown in FIG. 2.

The first post-signal-processing circuit 59a makes the first television monitor 60 display a moving normal image based on each field of image data of the inputted normal image signals. In the same way, the second post-signal-processing circuit 59b makes the second television monitor 61 display a moving fluorescence image based on each field of image data of the inputted fluorescence image signals. The third switch 58n changes a display in accordance with setting of the switches as aforementioned. When the fluorescence mode switch 73 is powered off, the moving normal image is displayed, as shown in FIG. 9, using the image signals stored in the fifth image memory 58k. When the fluorescence mode switch 73 is turned on, the moving fluorescence image is displayed using the image signals stored in the sixth image memory 58m in the case where the mode of two images being displayed side by side is not selected by the fluorescence mode display button 23a. If the mode is selected, the moving normal image and moving fluorescence image will be displayed side by side, as shown in FIG. 10, using the image signals stored in both of the fifth and sixth image memories 58k and 58m.

In display on any of the monitors, the second field of image signals is complemented by the arithmetical operation. Therefore, for example, compared with the case where the same signals as the first field of image signals are used as the second field of image signals, an apparent resolution can be improved because of the averaged and smoothed image data in time series.

The present disclosure relates to the subject matter contained in Japanese Patent Application No. P2005-000947, filed on Jan. 5, 2005, which is expressly incorporated herein by reference in its entirely.

What is claimed is:

1. An electronic endoscope system used for observing living tissues inside a body cavity, comprising:

a single imaging device configured to receive an optical image and output image signals obtained from the optical image;

an illuminating apparatus having a white light source emitting white light and an excitation light source that emits excitation light having a predetermined wavelength, the living tissues emitting autofluorescence when irradiated with the excitation light;

an image forming system configured to form the optical image of the living tissues illuminated with each of the white light and the excitation light on the imaging device;

a display device;

an image processing system that receives the image signals output from the single imaging device, the image processing system transforming the received image signals into signals which are displayable on the display device; and a control system configured to control the electronic endoscope system, wherein the control system controls the illuminating apparatus to illuminate the living tissues alternately with the white light and with the excitation light, wherein the control system controls the image processing system to obtain normal image signals when the living tissues are illuminated with the white light and fluorescence image signals when the living tissues are irradiated with the excitation light, wherein the image processing system employs image signals, obtained from an image, output from the single imaging device as a first field of image signals of an interlaced image, and employs image signals obtained by performing an arithmetical operation on image signals, from a plurality of images, output from the single imaging device as a second field of image signals of the interlaced image, and wherein one frame of each of the normal image and fluorescence image is configured with the first field of image signals and the second field of image signals.

2. The electronic endoscope system according to claim 1, wherein the image processing system employs image signals obtained by averaging the image signals obtained from the plurality of images output from the single imaging device as the second field of image signals of the interlaced image.

3. The electronic endoscope system according to claim 2, wherein the image processing system employs image signals obtained by averaging image signals obtained from an image output from the single imaging device in the last cycle and image signals obtained from an image output from the single imaging device in the cycle before the last cycle as the second field of image signals of the interlaced image.

4. The electronic endoscope system according to claim 3, wherein the image processing system comprises, for each of the normal image and the fluorescence image:

a first image memory configured to store image signals obtained from an image output from the single imaging device;

a delay system configured to receive the image signals output from the first image memory and to output the image signals with delay corresponding to one frame;

an averaging system configured to perform an averaging operation for the image signals output from the first image memory and the image signals output from the delay system, the averaging system outputting the averaged image signals by the averaging operation;

a second image memory configured to store the averaged image signals output from the averaging system; and a switch configured to select image signals to be output, from the image signals output from the first image memory and the averaged image signals output from the second image memory.

5. The electronic endoscope system according to claim 4, wherein the image processing system further comprises:

a pre-signal-processing system configured to process the image signals received from the single imaging device, the image signals processed by the pre-signal-processing system being input to the first image memory; and a post-signal-processing system, for each of the normal image and the fluorescence image, configured to transform the image signals output from the switch into signals which are displayable on the display device.

6. The electronic endoscope system according to claim 4, wherein the switch is configured to output, in an alternating manner, the image signals from the first image memory as the first field of image signals and the averaged image signals from the second image memory as the second field of image signals, and wherein the image processing system further comprises:

a third image memory configured to store one frame of the normal image configured with the first field of image signals and the second field of image signals output from the switch for the normal image;

a fourth image memory configured to store one frame of the fluorescence image configured with the first field of image signals and the second field of image signals output from the switch for the fluorescence image;

a second switch configured to output, in an alternating manner, the one frame of the normal image stored in the third image memory and the one frame of the fluorescence image stored in the fourth image memory; and a high-definition display device configured to display at least one of the one frame of the normal image and the one frame of the fluorescence image output from the second switch.

7. The electronic endoscope system according to claim 2, wherein the image processing system comprises, for each of the normal image and the fluorescence image:

a first image memory configured to store image signals obtained from an image output from the single imaging device;

at least one delay system configured to receive the image signals output from the first image memory and to output the image signals with a predetermined delay period;

an averaging system configured to perform an averaging operation for the image signals output from the first image memory and the image signals output from the at least one delay system, the averaging system outputting the averaged image signals by the averaging operation;

a second image memory configured to store the averaged image signals output from the averaging system; and a switch configured to select image signals to be output from the image signals output from the first image memory and the averaged image signals output from the second image memory.

8. The electronic endoscope system according to claim 7, wherein the image processing system further comprises:

a pre-signal-processing system configured to process the image signals received from the single imaging device, the image signals processed by the pre-signal-processing system being input to the first image memory; and a post-signal-processing system, for each of the normal image and the fluorescence image, configured to transform the image signals output from the switch into signals which are displayable on the display device.

9. The electronic endoscope system according to claim 7, wherein the switch is configured to output, in an alternating manner, the image signals from the first image memory as the first field of image signals and the averaged image signals from the second image memory as the second field of image signals, and wherein the image processing system further comprises:

a third image memory configured to store one frame of the normal image configured with the first field of image signals and the second field of image signals output from the switch for the normal image;

a fourth image memory configured to store one frame of the fluorescence image configured with the first field of image signals and the second field of image signals output from the switch for the fluorescence image;

a second switch configured to output, in an alternating manner, the one frame of the normal image stored in the third image memory and the one frame of the fluorescence image stored in the fourth image memory; and a high-definition display device configured to display at least one of the one frame of the normal image and the one frame of the fluorescence image output from the second switch.

10. The electronic endoscope system according to claim 1, wherein the image processing system comprises, for each of the normal image and the fluorescence image:
a first image memory configured to store image signals obtained from an image output from the single imaging device;
at least one delay system configured to receive the image signals output from the first image memory and output the image signals with a predetermined delay period;
an arithmetic system configured to perform said arithmetical operation for the image signals output from the first image memory and the image signals output from the at least one delay system, the arithmetic system outputting the modified image signals resulting from the arithmetical operation;
a second image memory configured to store the modified image signals output from the arithmetic system; and
a switch configured to select image signals to be output, from the image signals output from the first image memory and the modified image signals output from the second image memory.

11. The electronic endoscope system according to claim 10,
wherein the switch is configured to output, in an alternating manner, the image signals, from the first image memory as the first field of image signals and the modified image signals from the second image memory as the second field of image signals, and
wherein the image processing system further comprises:
a third image memory configured to store one frame of the normal image configured with the first field of image signals and the second field of image signals out put from the switch for the normal image;
a fourth image memory configured to store one frame of the fluorescence image configured with the first field of image signals and the second field of image signals output from the switch for the fluorescence image;
a second switch configured to output, in an alternating manner, the one frame of the normal image stored in the third image memory and the one frame of the fluorescence image stored in the fourth image memory; and
a high-definition display device configured to display at least one of the one frame of the normal image and the one frame of the fluorescence image output from the second switch.

12. The electronic endoscope system according to claim 1, wherein the illuminating apparatus includes a rotary shutter positioned in front of the white light source, the rotary shutter having a light transmitting area and a light blocking area, the white light intermittently illuminating the living tissues as the rotary shutter rotates.

13. The electronic endoscope system according to claim 12,
wherein the illuminating apparatus includes an excitation light source driver that intermittently turns on/off the excitation light source synchronously with the blocking/transmitting operation of the rotary shutter.

14. The electronic endoscope system according to claim 12,
wherein the rotary shutter is configured to be shifted together with a beam combiner to a position where the rotary shutter is not located along a path of the white light, the beam combiner combining light paths of the white light and of the excitation light when the rotary shutter and the beam combiner are located along the path of the white light.

15. The electronic endoscope system according to claim 1, wherein the image forming system comprises:
an objective lens configured to receive light from the living tissues and to form an image thereof; and
an excitation light cut filter provided between the objective lens and the imaging device,
wherein the excitation light cut filter eliminates the wavelength components equivalent to the excitation light from light directed to the imaging device from the objective lens.

16. The electronic endoscope system according to claim 15, wherein the excitation light source emits near-ultraviolet light.

17. The electronic endoscope according to claim 1, the image processing system comprising a delay circuit that outputs delayed image signals and being configured to average delayed image signals from a plurality of images output from the single imaging device as the second field of image signals of the interlaced image.

18. The electronic endoscope according to claim 1, the image processing system being configured to employ image signals not subjected to the arithmetical operation as the first field of the interlaced image.

19. The electronic endoscope according to claim 1, wherein the illuminating apparatus including a translatable dichroic mirror.

20. The electronic endoscope according to claim 1, the arithmetical operation comprising an averaging operation.

* * * * *